United States Patent
Doraiswamy et al.

(10) Patent No.: US 8,852,274 B2
(45) Date of Patent: Oct. 7, 2014

(54) COMPOSITE OPHTHALMIC DEVICES AND METHODS WITH INCIDENT LIGHT MODIFYING PROPERTIES

(75) Inventors: Anand Doraiswamy, Goleta, CA (US); Jensen Buck, Goleta, CA (US); Nahid Izadpanah, Goleta, CA (US)

(73) Assignee: Advanced Vision Science, Inc., Goleta, CA (US)

( * ) Notice: Subject to any disclaimer, the term of this patent is extended or adjusted under 35 U.S.C. 154(b) by 0 days.

(21) Appl. No.: 13/168,276

(22) Filed: Jun. 24, 2011

(65) Prior Publication Data
US 2012/0327362 A1    Dec. 27, 2012

(51) Int. Cl.
*A61F 2/16*   (2006.01)
*G02B 1/04*   (2006.01)
*G02B 1/10*   (2006.01)
*G02B 5/23*   (2006.01)
*G02C 7/10*   (2006.01)

(52) U.S. Cl.
CPC .............. *A61F 2/1613* (2013.01); *G02B 1/043* (2013.01); *G02B 1/10* (2013.01); *G02B 5/23* (2013.01); *G02C 7/105* (2013.01); *A61F 2/1659* (2013.01); *G02C 7/10* (2013.01)
USPC ............... 623/6.17; 351/159.49; 351/159.61

(58) Field of Classification Search
USPC ............ 351/159.03, 159.39, 159.61, 159.73, 351/159.49; 623/6.11–6.62
See application file for complete search history.

(56) References Cited

U.S. PATENT DOCUMENTS

| | | | |
|---|---|---|---|
| 3,269,267 A * | 8/1966 | Collins | 351/44 |
| 4,320,940 A * | 3/1982 | Mueller et al. | 351/44 |
| 4,594,179 A | 6/1986 | Harrah et al. | |
| 5,238,981 A * | 8/1993 | Knowles | 524/110 |
| 5,587,112 A | 12/1996 | Kauffman et al. | |
| 5,588,084 A | 12/1996 | Johnson | |
| 5,774,202 A | 6/1998 | Abraham et al. | |
| 6,102,543 A * | 8/2000 | Melzig | 351/159.61 |
| 7,214,749 B2 | 5/2007 | Miller et al. | |
| 2002/0001068 A1 | 1/2002 | Iwanczyk et al. | |
| 2005/0254003 A1* | 11/2005 | Jani et al. | 351/160 R |
| 2006/0025299 A1 | 2/2006 | Miller et al. | |
| 2006/0131761 A1 | 6/2006 | Chauhan et al. | |
| 2008/0218863 A1 | 9/2008 | Artsyukhovich et al. | |
| 2008/0265176 A1 | 10/2008 | Chauhan et al. | |
| 2009/0201462 A1* | 8/2009 | Gruber | 351/163 |
| 2009/0299081 A1 | 12/2009 | Porco, Jr. et al. | |
| 2011/0176103 A1* | 7/2011 | Iyer et al. | 351/169 |

FOREIGN PATENT DOCUMENTS

| | | |
|---|---|---|
| WO | 2005092876 A1 | 10/2005 |
| WO | 2005093459 A1 | 10/2005 |
| WO | 2006047768 A2 | 5/2006 |
| WO | 2007057782 A2 | 5/2007 |
| WO | 2007139749 A2 | 12/2007 |
| WO | 2009143054 A2 | 11/2009 |

OTHER PUBLICATIONS

Visible Spectrum, http://en.wikipedia.org/wiki/Visible_spectrum, Mar. 1, 2011.

* cited by examiner

*Primary Examiner* — Darryl J Collins
(74) *Attorney, Agent, or Firm* — Whyte Hirschboeck Dudek S.C.

(57) ABSTRACT

A composite ophthalmic device comprising an ophthalmic structure, means or lens having a photo-shifting material deployed thereon or therewithin so as to up-shift or down-shift the amplitude, wavelength (or both) of incident radiation into the visible wavelength range.

5 Claims, 6 Drawing Sheets

COMPOSITE OPHTHALMIC DEVICES AND METHODS WITH INCIDENT LIGHT MODIFYING PROPERTIES

This invention relates to optical devices such as ophthalmic devices or lenses having incident light-modifying or incident radiation-modifying properties. More specifically, this invention relates to transparent ophthalmic polymer structures which modify, in controlled or controllable fashion, the frequency, amplitude (or both) of incident light passing there through. Both upward-shifting and downward-shifting of incident light frequency, amplitude or both are included in this invention. The inclusion of the upward-shifting and/or downward-shifting of incident light frequency, amplitude (or both) increases the intensity of visible-to-the-human-eye light exiting the optical device. A particular preferred application of this invention is intraocular lenses (IOLs), having such incident light modifying properties as are described herein.

The visible-to-the-human eye light spectrum is delimited on one end by the high energy, high frequency, short wavelength, ultra-violet band (UV) and on the other by the lower-energy, shorter frequency, and longer wavelength infrared band. Generally speaking, the visible light spectrum spans light having wavelength in the range of about 390 nm to about 800 nm. Desirably an ophthalmic device employs the entire visible light spectrum and, if possible, adjacent portions of the UV and infrared spectra which have shorter and longer wavelengths, respectively, than visible light. An ophthalmic device that converts high energy harmful UV incident light to the safe and useable visible spectrum range enhances both visual acuity and visual contrast under both mesopic and photopic conditions. An ophthalmic device that converts the low energy infrared incident light to the visible spectrum provides improved scotopic vision (improved night or low-light visibility).

The visible-to-the-human eye light spectrum is delimited on one end by the high frequency, short wavelength, ultra-violet band (UV) and on the other by lower-energy, longer wavelength, lower frequency, and infrared band. Generally speaking, the visible light spectrum spans light or radiation having wavelength in the range of about 390 nm to about 800 nm. Desirably an ophthalmic device employs the entire visible light spectrum and, if possible, adjacent portions of the UV and infrared spectra which have shorter spectrum and longer wavelengths, respectively, than the visible light. Conversion of high energy UV spectral bandwidth light to the useable visible spectrum range by an optical lens provides enhanced visual acuity and visual contrast to a person having an ophthalmic device which produces that conversion. Conversion of infrared wavelength incident radiation to the visible spectrum provides, e.g., improved night or low light visibility.

BRIEF SUMMARY OF THE INVENTION

Briefly, in one aspect, the present invention is a composite lens, ophthalmic device, or optical device having a visually transparent lens body, lens means or optic, the lens body, lens means or optic structure having a photosensitive material coated thereon, dispersed therewithin, sandwiched therein, embedded therein or otherwise operatively associated with the lens body so as to interact with incident radiation passing therethrough, or reflected therefrom, to increase or decrease one or both of the amplitude or available frequency of said radiation and thereby to broaden the span of the electromagnetic spectrum which is visible to the eye. It is to be understood that both up-shift and/or down-shift of incident radiation frequency or amplitude (hereinafter referred generally to as "photo-shifting" or "photo-modifying") to visible are within the scope of this invention.

Thus, in one aspect, this invention is a transparent-to-visible-light lens body or structure having photo-shifting or photosensitive material, compound or polymer disposed or deployed in operative association therewith so that radiation incident upon and passing into or through the lens body (and thus the photo-shifting material zone or co-polymer) has one or both of its amplitude or wavelength up-shifted or down-shifted, so as to enhance or increase visible light availability.

In another aspect, the present invention is a method of broadening the electromagnetic spectrum or spectral bandwidth within the visible range comprising the steps of:

providing an ophthalmic device having a photosensitive material in operable associate therewith;

exposing the optical device to incident radiation having a wavelength adjacent to but at least slightly above or below the wavelength range of visible light;

permitting the device to up-shift or downshift the wavelength of the incident radiation of the previous step into a wavelength range of visible light.

BRIEF DESCRIPTION OF THE FIGURES

This invention will now be illustrated and exemplified by the attached figures and detailed description which follows. The figures and description are intended to be illustrative and not limiting of the claims which follow.

Thus, there is shown:

FIG. 7 is an enlarged view of a portion of the lens shown in FIG. 6. In FIG. 7 wavefronts 12 are shown to be internally reflected.

DETAILED DESCRIPTION OF THE INVENTION

Figure 1:
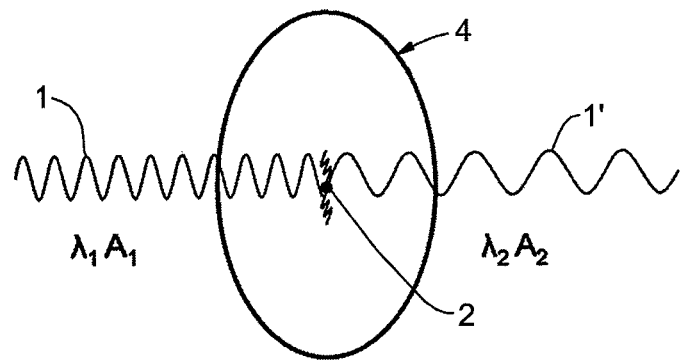
FIG. 1 illustrates schematically the interaction between incident radiation 1 and an operatively (so as to interact with the incident radiation 1-1', the 1' being used to indicate the shifted or modified radiation wavefront) lens-deployed compound, photo-sensitive or photo-shifting zone, layer, coat or molecule cluster 2. Molecular cluster 2 is embedded within composite lens 4. It is to be understood that lens 4 is a schematic lens body, optic or operant optical means of an ophthalmic device such as an IOL, phakic lens, or contacts and may have additional appurtenant structures or features e.g., haptics which are not shown. Incident radiation or wavefront 1 has wavelength and amplitude $\lambda_1$, and $A_1$ prior to interaction with photo-shifter material 2 and wavelength and amplitude $\lambda_2$ and $A_2$ after interaction. Incident radiation 1-1' wavelength or amplitude may be separately and independently shifted or shifted together. As is shown, radiation wavefront passes through composite lens 4 i.e., the lens is transparent with respect thereto. The photo-shifting material or component embedded in the intraocular lens may amplify or reduce the wavelength and amplitude of the incident light. i.e. $\lambda_1 < \lambda_2 A_1 < A_2$ or $\lambda_1 > \lambda_2 \lambda A_1 > A_2$ so that the modified light, e.g., 1', falls within the visible spectrum even if the incident light 1, did not.
Figure 2:
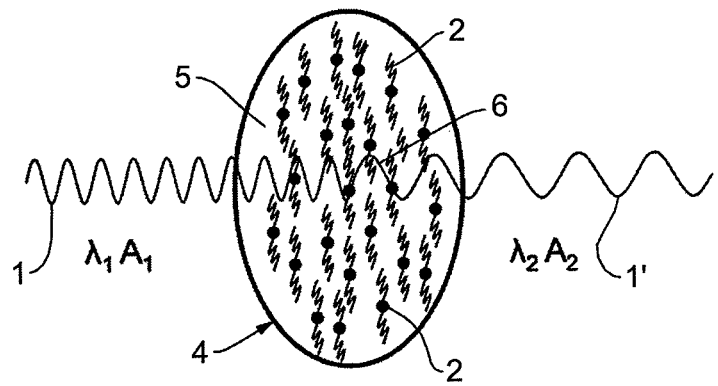
FIG. 2 shows a distribution of photo-sensitive material 2 distributed as a coating on one or both major surfaces 5,6 of lens 4 or within the bulk of lens 4.
Figure 3:
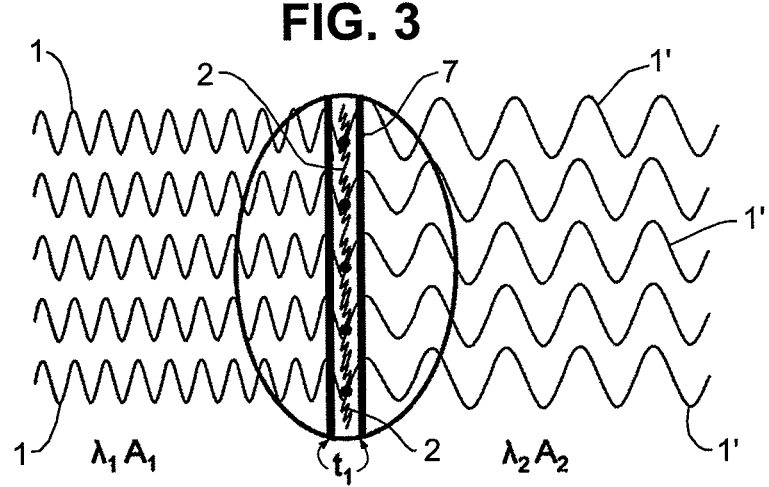
FIG. 3 illustrates a "sandwich" or zone 7 deployment of photo-shifting material 2 within lens 4. A series of incident and modified light wavefronts 1-1' are shown by the brackets. Zone 7 has a thickness of $t_1$.
Figure 4:
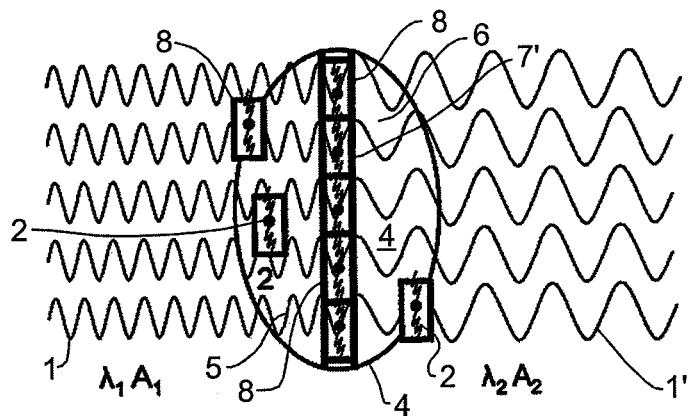
FIG. 4 illustrates zones, clusters, or cells 8 of photo-shifting or modifying material 2, material 2 being deployed in sandwich 7', anteriorly, posteriorly 5,6 or within the bulk 8 of lens 4.
Figure 5:
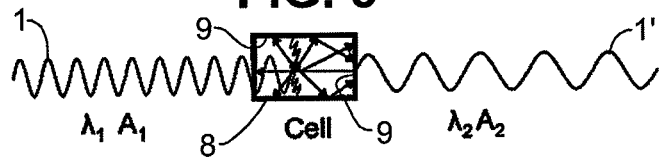
FIG. 5 illustrates the use of cells 8 as in FIG. 4 wherein reflective or partially reflective surfaces 9 are used to filter some or a majority of incident light or radiation 1 and emitted light or radiation 1'. Each cell may contain partially or highly reflective surfaces on all faces except the transmission face. All faces, particularly the transmission face (toward the anterior side) will be transparent to incident light on the front face but reflective on the rear face. Upon excitation at the appropriate wavelength, the photosensitive material will separately, independently, or concurrently convert the incident light from $\lambda_1$, $A_1$ to $\lambda_2$, $A_2$. All converted (amplified or reduced) emitted/scattered light will be reflected back from all faces of the cell and transmitted via the posterior non-reflective face as $\lambda_2$, $A_2$.

In summary, this invention is the deployment of an amplitude or frequency-shifting material or coating on or within a lens body, optical or ophthalmic prosthetic device or lens optic to broaden the spectrum of incident radiation that falls within the visible range. As is noted above, a lens constructed according to the parameters of this invention will provide to a person using such a lens either or both of enhanced night vision or improved visual acuity or contrast by virtue of UV light energy down-shift (in frequency) to visible or infrared light up-shift to visible in frequency, amplitude or both.

A composite lens of this invention comprises a conventional visible-light-transmissive lens body or optic and a photo-shifter material operatively deployed thereon or, therewithin. Conventional lens body materials are well known to persons skilled in this art but include, without limitation, both hydrophilic and hydrophobic acrylic polymers and silicone materials. It will be appreciated that a high degree of transmissivity to visible light is the primary requirement of this bulk or working structure lens material. Specific lens structures contemplated by this invention include implantable ophthalmic lenses, e.g., intraocular lenses. Also contemplated are other lens structures such as contacts lenses, and phakic lenses. One skilled in this art will appreciate the many and varied applications of this invention within the vision correction art.

At present, several, but not necessarily all photo-shifting, as in wavelength or amplitude increasing or decreasing materials, have been identified. These materials are sometimes referred to as photo-shifting dyes. Specific preferred wavelength-shifting or wavelength-changing materials include 3-hydroxyflavone (3-HF), 2,5 bis(5-tertbutyl-2-benzoxazolyl) thiophene (BBOT), 2,5-diphenyloxyzol (DPO), polyvinyl toluene-based materials, and quantum wells/semiconductor materials (In Ga As/InP).

Without wishing to be bound by a theory, it is believed that materials which exhibit either a Stokes or anti-Stokes shift or electromagnetic absorption/emission have particular applicability to the present invention. (This aspect of the invention is discussed in greater detail in the Examples). Thus Stokes and anti-Stokes absorption/emission (fluorescence) materials generally are deployed, according to this invention to obtain the enhanced visual acuity discussed herein. Enhanced visual acuity is obtainable in practice of this invention by modifications of intraocular lenses (IOLs), corneal inlays, glasses (i.e., spectacle lenses), contact lenses, and essentially any optical appliance or device which helps the eye to see. Presbyopia correction is a primary application of optical devices or prostheses of this invention.

An intraocular lens comprising of a photosensitive material or component that can shift the transmitted wavelength or amplitude, or both of the incident light. Applications primarily include wavelength up-conversion of high-energy ultraviolet wavelength to safe and useful visible wavelength for improved visual acuity and contrast. Applications may also include down-conversion of infra-red wavelength to visible spectrum for improved night vision.

The material or component may be confined to a particular zone within the intraocular lens or scattered/distributed across the lens surface or bulk.

Figure 6:
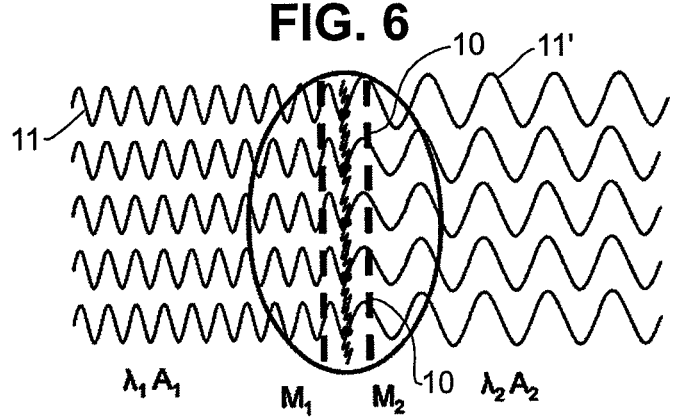
FIGS. 6 and 7 illustrate the use of a photosensitive material deployed in a systematic pattern, filter, or grid 10, so that only selected radiation 11 modified to $\lambda_2$ and $A_2$ emerges therefrom.
Figure 7:
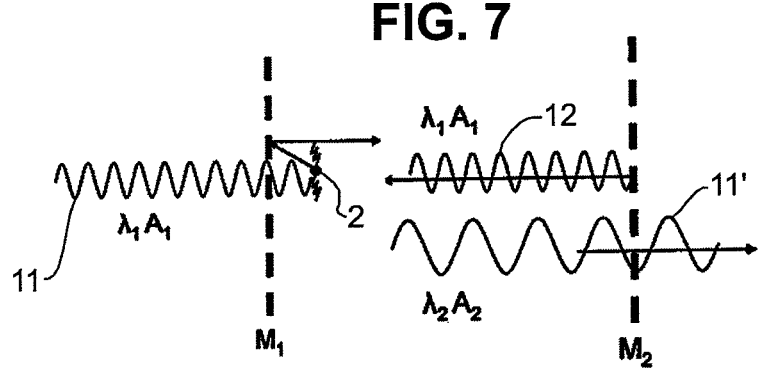

The photosensitive material may be confined as a sandwich between two filters in the anterior and posterior parts of the lens as shown in FIG. 6. The photosensitive zone of the lens may be defined by a selective thickness, $M_1$-$M_2$. The anterior and posterior filter may limit the frequency and amplitude of the transmitted light. This will allow control over the incoming wavelength for stimulating the photo-shifting material and control over the excited/transmitted wavelength past the posterior filter. In this manner wavelength frequency/amplitude can be both controlled and modified.

The concentration and type of wavelength-shifting material may be distributed across or through the bulk or located on surface of the optic in a systematic pattern to correct aberrations including coma, spherical aberration, and astigmatism.

The concept may also be applied to contact lenses and phakic lenses and a variety of intraocular lenses.

The terminology "operatively associated" is used in this application to be broadly interpreted to refer to the relationship between an optical device such as a lens body or optic and a photo-shifting material which provides photo-shifting as described herein.

PROPHETIC EXAMPLE

In one aspect the present invention employs an optical material which exhibits what is referred to as a Stokes shift or its related concept, anti-Stokes shift.

Stokes shift is the difference (in wavelength or frequency unites) between positions of the band maxima of the absorption and emission spectra (fluorescence and Raman being two examples) of the same electronic transition.

When a system (be it a molecule or atom) absorbs a photon, it gains energy and enters an excited state. One way for the system to relax is to emit a photon, thus losing its energy. When the emitted photon has less energy than the absorbed photon, this energy difference is the Stokes shift. If the emitted photon has more energy, the energy difference is called an anti-Stokes shift. For example, energy to produce an anti- Stokes shift can come from dissipation of thermal phonons in a crystal lattice, cooling the crystal in the process. Yttrium oxysulfide doped with gadolinium oxysulfide is a common industrial anti-Stokes pigment, absorbing in the near-infrared and emitting in the visible portion of the spectrum.

Figure 8:
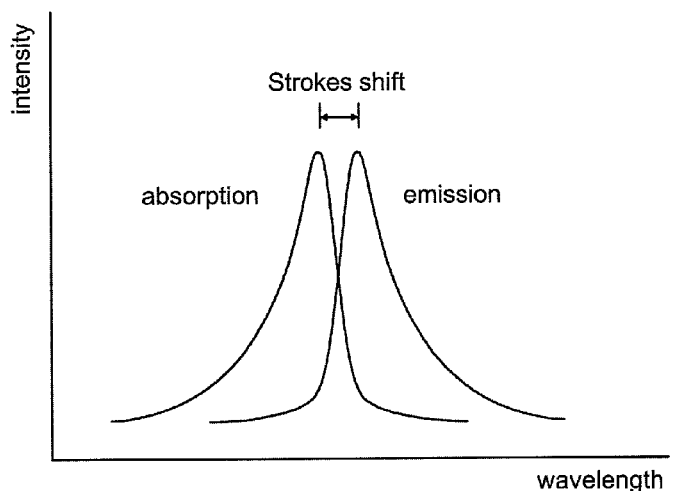
FIG. 8 illustrates the concept of Stokes shift and is discussed in the Prophetic Examples below.

Stokes fluorescence is the re-emission of longer wavelength photons (lower frequency or energy) by a molecule that has absorbed photons of shorter wavelengths (higher frequency or energy). Both absorption and radiation (emission) of energy are unique characteristics of a particular molecular structure. If a material has a direct bandgap in the range of visible light, the light shining on it is absorbed, causing electrons to become excited to a higher energy state. The electrons remain in the excited state for about $10^{-8}$ seconds. The electron returns to the ground state and energy is emitted. Stokes-shift from higher energy, shorter wavelength UV light is shown in FIG. 8. [1]

[1] Paragraphs [0026]-[0028] partially based upon information at http://en.wikipedia.org/wiki/Stokes_shift visited on Jun. 15, 2011.

Electromagnetic radiation that can be detected by the human eye, i.e., visible light or simply "light" generally has a wavelength (λ) falling in the range of 390 to about 750 nm, inversely corresponding to a frequency (ν) in the range of 400 to 790 Thz.

Falling just below (in terms of wavelength) and just above visible light are those portions of the electromagnetic radiation spectrum referred to as ultraviolet (wavelength about 10 nm to 400 nm) and near infrared (wavelength about 750 nm to about 1,500 nm), respectively.

Thus by application of a transparent Stokes-shifting material to a visually transparent substrate, e.g., a lens, as is described above, near infrared electromagnetic radiation not otherwise visible to the human eye has its wavelength shortened upon emission to produce a human eye-visible response. Conversely application of an anti-Stokes shifting material to a transparent substrate lengthens the wavelength of impinging, not otherwise visible ultra-violet light, to produce, upon emission, visually perceivable radiation.

Illustrating the above, a lens, spectacle, ophthalmic device, or contact lens having a coating or inclusion of wavelength down-shifting material on or in a hydrophobic acrylic lens body to increase the visibility of objects in low light conditions.

Figure 9:
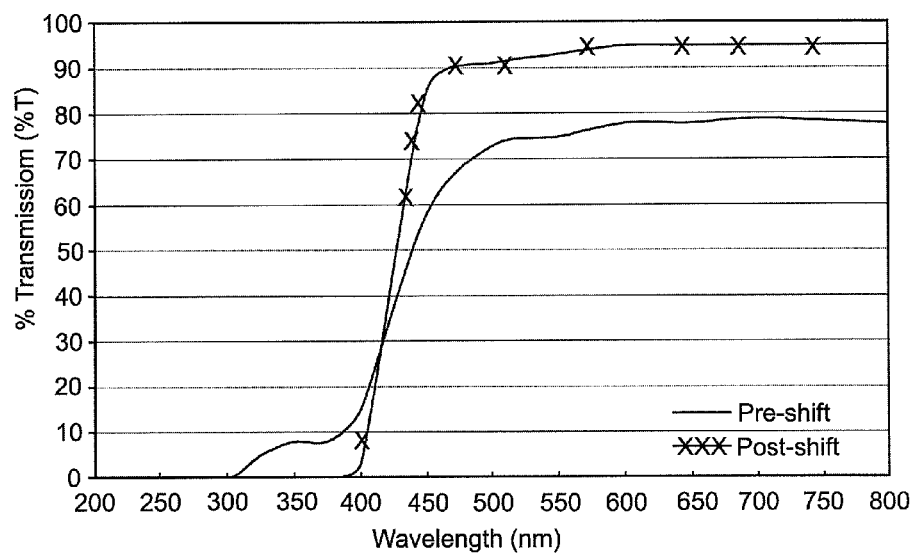
FIGS. 9 and 10 illustrate, using a wavelength versus % transmission curve, the downshift in energy to longer wavelength visible to light e.g., UV/blue, incident radiation to longer wavelength visible light.
Figure 9:
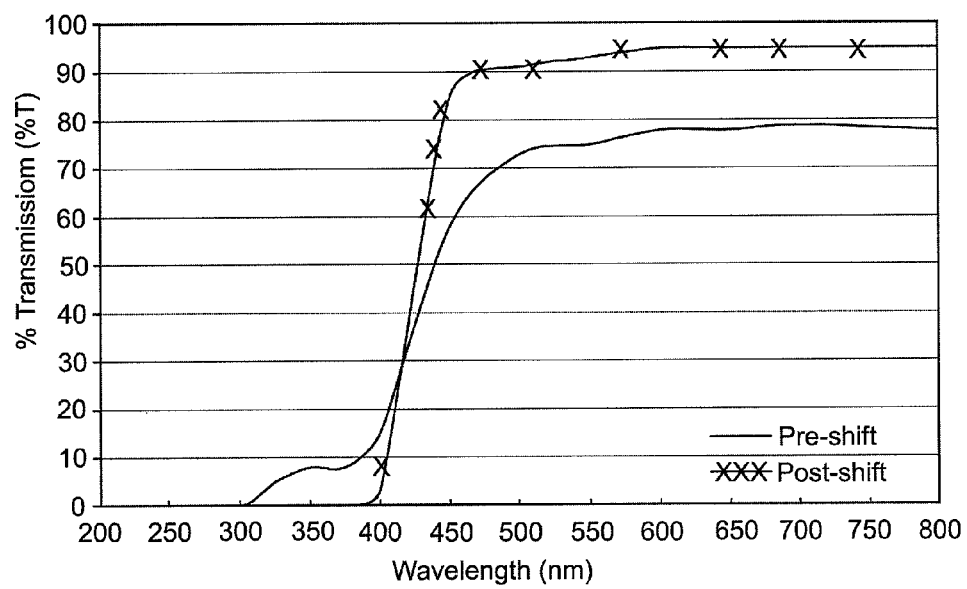
Figure 10:
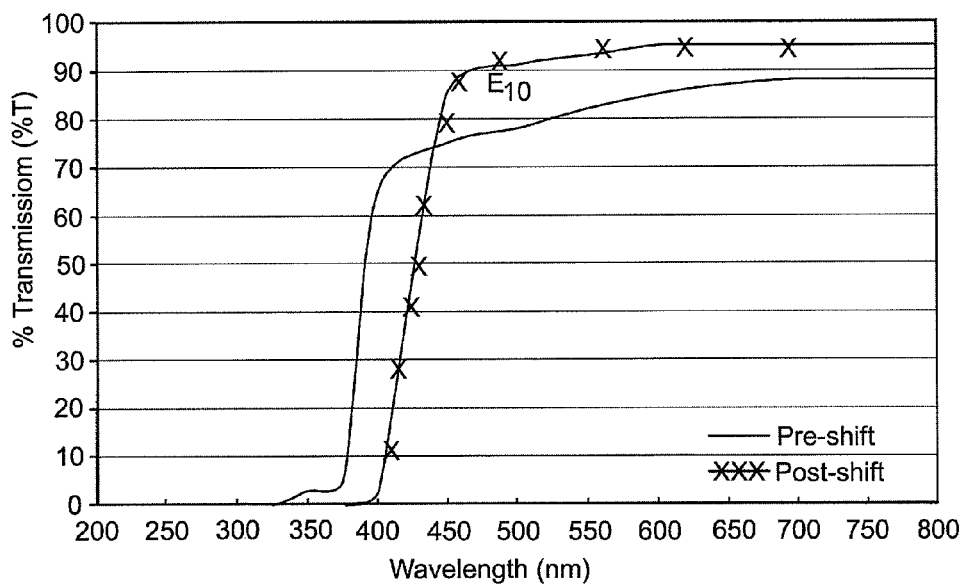

Referencing FIGS. 9 and 10, wavelength vs. % transmission hypothetical curves are shown. In FIGS. 9 and 10 conventional ophthalmic device (pre-shift) and post-shift ophthalmic device transmission curves are shown. The post-shift transmission curve is marked with "x"s. The area between the post-shift curves and the pre-shift curves (designated $E_9$ and $E_{10}$, respectively), is energy transformed into the visible light spectrum from the non-visible (by the human eye) ultraviolet/blue spectrum by use of this invention. This is an anti-Stokes shift.

Figure 11:
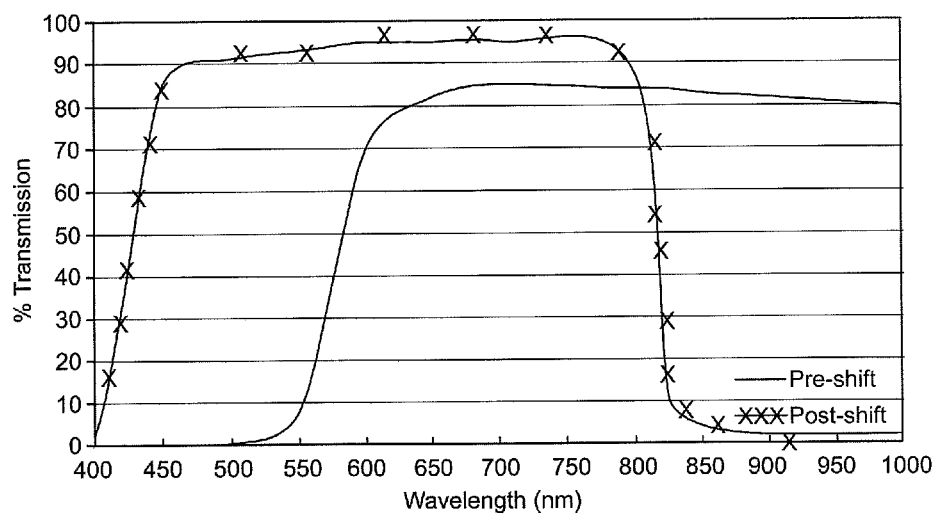
FIG. 11 illustrates wavelength versus % transmission curve, an upshift in energy to shorter wavelength visible light, e.g., near IR or TR, incident to short wavelength visible light.

Referring to FIG. 11, wavelength vs. % transmission hypothetical curves are shown. In FIG. 11 a conventional ophthalmic device (pre-shift) and ophthalmic device of this invention (post-shift) wavelength vs. % transmission curves are shown. The post-shift curves are shown with "X"s. The area between the post-shift curve and the pre-shift curve at pre-shift wavelengths about 800 nm is energy transferred into the visible light spectrum from the non-visible (to the human eye) IR/near IR spectrum by use of this invention. This is what is referred to as a Stokes shift.

Figure 12:
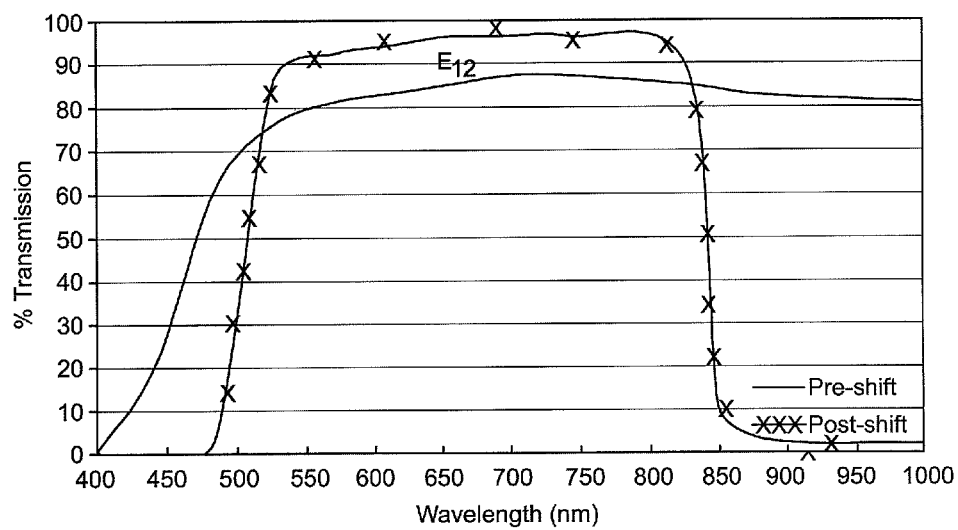
FIG. 12 illustrates using a wavelength versus % transmission curve, the situation where wavelength/amplitude are upshifted and downshifted in the same optical device.

In FIG. 12 there is shown a conventional device (pre-shift) and a device of this invention (post-shift) wavelength vs. % transmission curves for the situation where wavelength upshift and downshift occurs in the same device. Specifically, by use of this invention, transfer of energy is shown (designated E12) into the human eye visible spectrum range of 400 nm to 800 nm from both the longer wavelength IR spectrum and the shorter wavelength UV/blue spectrum.

Figure 13A:
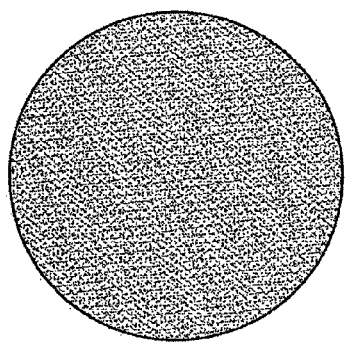
FIGS. 13A-13D illustrates exemplary operative associations, e.g., lens examples, between wavelength-shifting materials or zones and specific optical bodies or optical means.
Figure 13B:
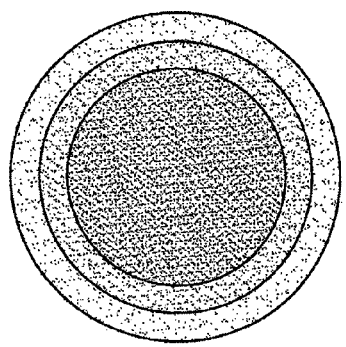

FIGS. 13A-13D illustrate optical devices (e.g., corneal inlays/onlays, IOLs, contact lenses) having wavelength-shifting materials used in association therewith. FIG. 13A shows a uniform coating of wavelength-shifting material on one side of the optical body. FIG. 13B illustrates an optical body having a wavelength-shifting interior zone (the darker area) adapted to be used with changing pupil size.

Figure 13C:
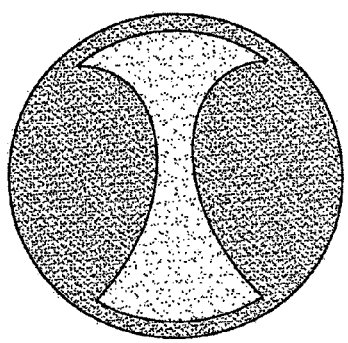

FIG. 13C illustrates a possible deployment of this invention in a cylindrical configuration when the user of a lens having this optic body ahs astigmatism.

Figure 13D:
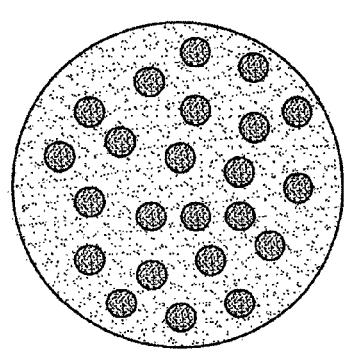

FIG. 13D shows randomly deployed wavelength-shifting zones in the optic body (darker dots) providing a pin-hole effect useful for lens wearers/users with certain types of ophthalmic infirmities. It is to be understood that only the optic bodies or lenses of the ocular device are shown in FIGS. 13A-13D, these being omitted structures, e.g., haptics, depending upon the particular intended application for the lens body or optic.

The above description and attached figures are intended to be illustrative and not limiting of the above invention which is defined in the following claims. One skilled in the art of polymer chemistry, particularly, ophthalmic device polymer chemistry, will readily appreciate and be knowledgeable regarding the numerous techniques used to create polymer coatings, bulk distribution or localized zones or inclusions of one polymeric material in or on another. Depending upon the specific application, particularly ophthalmic device polymer chemistry, copolymer mixtures, or simply a polymer coat on a polymer substrate (e.g., the lens body) will be created. It is within the knowledge of one skilled in the ophthalmic materials art to select the synthetic route to produce a composite device of this invention.

What is claimed is as follows:

1. An intraocular lens having a lens body and operatively associated therewith, a photosensitive material comprising a wavelength-shifting dye, the lens body being transparent with respect to incident radiation, the photosensitive material having the ability to up-shift or down-shift incident radiation-frequency or amplitude, or both frequency and amplitude so that the amplitude, the frequency or both the amplitude and the frequency of the incident radiation are modified by the photosensitive material so that the incident radiation falls within the visible spectrum.

2. A lens according to claim 1, wherein the lens is a composite structure comprising a visible light-transparent lens body which is operatively associated with a coating of the photosensitive material.

3. A lens according to claim 1, wherein the lens is a composite structure comprising a visible light-transparent lens body which is operatively associated with a discrete zone of a photosensitive material.

4. A lens according to claim 1, wherein the lens is a composite structure comprising a sandwich of a photosensitive material placed between two lens components, the lens components being transmissive to visible light.

5. A method of increasing the spectral band-width in the visible range of radiation incident upon an intraocular lens comprising the steps of:
providing an intraocular lens having a photosensitive material comprising a wavelength-shifting dye in operable associate therewith;

exposing the intraocular lens to incident radiation having a wavelength adjacent to but at least slightly above or below the wavelength range of visible light;

permitting the lens to up-shift or down-shift the wavelength of the incident radiation of the previous step into a wavelength range falling within that of visible light.

\* \* \* \* \*

UNITED STATES PATENT AND TRADEMARK OFFICE
CERTIFICATE OF CORRECTION

| | | |
|---|---|---|
| PATENT NO. | : 8,852,274 B2 | Page 1 of 1 |
| APPLICATION NO. | : 13/168276 | |
| DATED | : October 7, 2014 | |
| INVENTOR(S) | : Anand Doraiswamy, Jensen Buck and Nahid Izadpanah | |

It is certified that error appears in the above-identified patent and that said Letters Patent is hereby corrected as shown below:

In the Drawings
Sheet 3, Fig. 8, replace "Strokes" with --Stokes--

Signed and Sealed this
Twenty-fourth Day of March, 2015

Michelle K. Lee
*Director of the United States Patent and Trademark Office*